(12) United States Patent
Wrasidlo et al.

(10) Patent No.: US 8,304,408 B2
(45) Date of Patent: Nov. 6, 2012

(54) WNT SIGNALING INHIBITORS, AND METHODS FOR MAKING AND USING THEM

(75) Inventors: Wolfgang Wrasidlo, La Jolla, CA (US); Catriona H. Jamieson, La Jolla, CA (US); Dennis Carson, La Jolla, CA (US); Tadeusz F. Molinski, La Jolla, CA (US); Desheng Lu, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 238 days.

(21) Appl. No.: 12/600,996

(22) PCT Filed: May 15, 2008

(86) PCT No.: PCT/US2008/063742
§ 371 (c)(1),
(2), (4) Date: Apr. 12, 2010

(87) PCT Pub. No.: WO2008/147713
PCT Pub. Date: Dec. 4, 2008

(65) Prior Publication Data
US 2010/0203113 A1      Aug. 12, 2010

Related U.S. Application Data

(60) Provisional application No. 60/940,060, filed on May 24, 2007.

(51) Int. Cl.
*A61K 31/35* (2006.01)
*A61P 35/02* (2006.01)
(52) U.S. Cl. .............. 514/212.06; 514/212.07
(58) Field of Classification Search ............. 514/212.06, 514/212.07
See application file for complete search history.

(56) References Cited

U.S. PATENT DOCUMENTS

| 5,591,740 | A | 1/1997 | Chipman et al. |
| 6,197,954 | B1 | 3/2001 | Horne et al. |
| 6,211,361 | B1 | 4/2001 | Horne et al. |
| 7,193,079 | B1 | 3/2007 | Tepe |

FOREIGN PATENT DOCUMENTS

EP    1106180 A1    6/2001

OTHER PUBLICATIONS

Wan Yongqin, et al. (2004) Synthesis and target identification of hymenialdisine analogs, Chemistry & Biology vol. 11, Issue: 2, Publisher: Elsevier, pp. 247-259.
Vasudha Sharma, et al. (2004) Potent inhibition of checkpoint kinase activity by a hymenialdisine-derived indoloazepine, Bioorganic & Medicinal Chem. Letters 14:4319.
Laurent Meijer, et al. (2000) Inhibition of cyclin-dependent kinases, GSK-3beta and CK1 by hymenialdisine, a marine sponge constituent, vol. 7(1):51-63.
Athina Nickitas-Etienne, International Preliminary Report on Patentability Chapter I (IB/373), Nov. 29, 2009, WIPO.
Bum Soo Kim, Initial Publication with ISR (A1 49/2008), Oct. 22, 2008, ISA/KR, WIPO.
Bum Soo Kim, Written Opinion of the International Search Authority, Oct. 22, 2008, ISA/KR, WIPO.
Darko Courman (2001) Inhibition of the G2 DNA Damage Checkpoint and of Protein Kinases Chk1 and Chk2 by . . . Alkaloid Debromohymenialdisine, J. Biol. Chem. 276:17914-17919.
[No Author] EMB Biosciences, Calbiochem Biologies (2006) Glycogen Synthase Kinase-3: Its Signaling Role in Development and Disease 32:1-23.

*Primary Examiner* — Bruck Kifle
(74) *Attorney, Agent, or Firm* — Gavrilovich, Dodd & Lindsey LLP; Gregory P. Einhorn

(57) ABSTRACT

The invention provides dBHD-based compositions and dBHD analog compositions, and pharmaceutical compositions comprising them, e.g., in the form of liposomes and nanoparticles comprising them, and methods of making and using them. In one embodiment, these dBHD analogs are used to inhibit a dysfunctional stem cell and/or a cancer (tumor) stem cell.

9 Claims, 11 Drawing Sheets

WNT SIGNALING INHIBITORS, AND METHODS FOR MAKING AND USING THEM

STATEMENT AS TO FEDERALLY SPONSORED RESEARCH

This invention was made with government support under Grant No. CA85602 awarded by the National Institutes of Health. The government has certain rights in this invention.

CROSS-REFERENCE TO RELATED APPLICATIONS

This United States utility patent application is the §371 national phase of PCT international patent application no. PCT/US2008/063742 having an international filing date of May 15, 2008, which claims benefit of priority to U.S. Provisional Patent Application Ser. No. 60/940,060, filed May 24, 2007. The aforementioned applications are expressly incorporated herein by reference in their entirety and for all purposes.

TECHNICAL FIELD

This invention generally relates to biochemistry, cell and tumor biology and medicine. The invention provides compositions comprising debromohymenialdesine (dBHD) and dBHD analogs, and pharmaceutical compositions comprising them, and methods for inhibiting cancer cells, including cancer (tumor) stem cell growth, but not normal stem cell growth. In alternative embodiments, the compositions and methods of the invention, including the dBHD-based compositions and dBHD analog compositions of the invention, and the pharmaceutical compositions comprising them, are used to treat, prevent or ameliorate (including slowing the progression of) a cancer, e.g., a prostate cancer or a leukemia. In one aspect, dBHD-based compositions and dBHD analog compositions of this invention are used to inhibit beta-catenin, a key protein in the Wnt-signaling path.

BACKGROUND

Wnt proteins form a family of highly conserved secreted signaling molecules that regulate cell-to-cell interactions during embryogenesis. The name "Wnt" was coined as a combination of Wg (wingless) and Int. The wingless gene had originally been identified as a segment polarity gene in *Drosophila melanogaster* that functions during embryogenesis, and also during adult limb formation during metamorphosis. The Int genes were originally identified as vertebrate genes near several integration sites of mouse mammary tumor virus (MMTV). The Int-1 gene and the wingless gene were found to be homologous, with a common evolutionary origin evidenced by similar amino acid sequences of their encoded proteins.

Many Wnt genes in the mouse have been mutated, leading to very specific developmental defects. As currently understood, Wnt proteins bind to receptors of the Frizzled and LRP families on the cell surface. Through several cytoplasmic relay components, the signal is transduced to β-catenin, which then enters the nucleus and forms a complex with TCF (T Cell Factor) to activate transcription of Wnt target genes.

Wnt genes and Wnt signaling also have been implicated in cancer. Autocrine Wnt signaling within tumor cells has been shown to promote tumorigenesis by enhancing tumor cell proliferation and survival. The deregulation of this pathway can be detected in numerous cancers, resulting in the accumulation of beta-catenin (β-catenin) in the cell nucleus where it interacts with transcription factors of the LEF/TCF family and induces transcription of wnt target genes. There is mounting evidence of Wnt pathway activation during prostate tumorigenesis. Further, beta-catenin functions as a coactivator for the androgen receptor. The frequent dysregulation of wnt in prostate cancers suggests that this pathway is suitable for therapeutic intervention.

Current therapy for advanced prostate cancer relies on traditional cytotoxic agents with limited effects. This has spurred an increased interest in understanding the mechanisms of prostate cancer tumorigenesis at the molecular level with the aim of finding specific molecular targets for intervention. Abnormal Wnt signaling in the development and progression of human prostate cancer has been demonstrated and the molecular details of various aberrant feed back mechanisms are being elucidated. From these investigations, including the accumulation of beta-catenin in the cancer cell nucleus, its complexation with the TcF family transcription factors to activate a variety of cancer-associated genes, Wnt has been associated with tumor progression, including metastatic lesions of the bone. Compounds that disrupt this path at the transcription level are being sought for the development of new products for therapeutic use.

SUMMARY

The invention provides compounds (compositions) comprising debromohymenialdesine (dBHD), or (4Z)-4-(2-amino-5-oxo-3,5-dihydro-4H-imidazol-4-ylidene)-4,5,6,7-tetrahy-dropyrrolo(2,3-c)azepin-8(1H)-one (see compound I, FIG. 1), and dBHD analogs, for example, as illustrated in FIG. 5.

The invention provides compounds (compositions) having a formula:

(a) debromohymenialdesine (dBHD), or (4Z)-4-(2-amino-5-oxo-3,5-dihydro-4H-imidazol-4-ylidene)-4,5,6,7-tetrahy-dropyrrolo(2,3-c)azepin-8(1H)-one (see compound I, FIG. 1);

(b) comprising a compound having the formula:

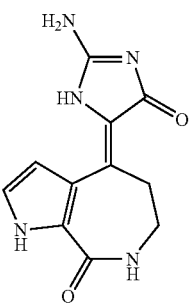

(c) as set forth in FIG. 5, or having the formula:

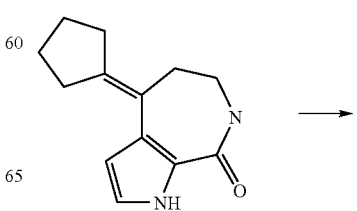

-continued

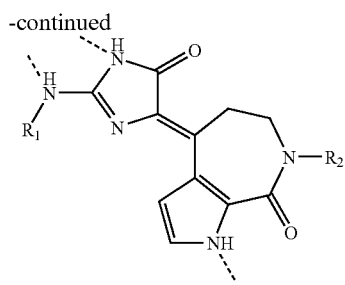

wherein R₁ and/or the R₂ group are independently selected from the group consisting of hydrogen, halo, hydroxy (—OH), thiol (—SH), cyano (—CN), formyl (—CHO), alkyl, heteroalkyl, heteroalkenyl, heteroalkynyl, haloalkyl, alkene, alkenyl, alkynyl, aryl, substituted aryl, amino, nitro (—NO₂), alkoxy, haloalkoxy, thioalkoxy, alkanoyl, haloalkanoyl and carbonyloxy, or having the formula

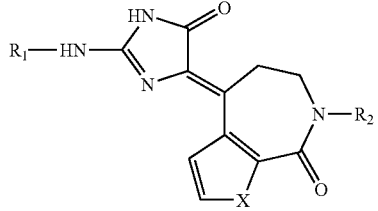

X = NH, O, S, CH2
R1 = alkyl group, alkoxy group, allycyclic, heterocyclic, aromatic
R2 = R1 independenly or wherein X is selected from the group consisting of NH, O, S and CH₂, and R₁ and/or the R₂ group are independently selected from the group consisting of hydrogen, halo, hydroxy (—OH), thiol (—SH), cyano (—CN), formyl (—CHO), alkyl, heteroalkyl, heteroalkenyl, heteroalkynyl, haloalkyl, alkene, alkenyl, alkynyl, aryl, substituted aryl, amino, nitro (—NO₂), alkoxy, haloalkoxy, thioalkoxy, alkanoyl, haloalkanoyl and carbonyloxy, or (d) the formula of (c), wherein the alkyl, haloalkyl, alkene, alkenyl in both or either of the R₁ and/or the R₂ groups is (independently) at least 1, 2, 3, 4, 5, 6, 7, 8, 9, 10, 11, 12, 13, 14, 15 or 16 or more carbons in length;

(e) the formula of (a), (b), (c) or (d), wherein the heterocyclic moiety in both or either of the R₁ and/or the R₂ groups (independently) comprises a 5 membered ring or a 6 membered ring system; or (f) the formula of (e), wherein 5 membered ring system comprises an imidazole, thiazole, triazole or oxadiazole, or the 6 membered ring system comprises a pyridine, a pyrimidine or a pyrazine.

The invention also provides pharmaceutical compositions comprising these compounds, and methods for making and using them, for example, methods and uses for inhibiting the growth of cancer cells, dysfunctional stem cells and cancer (tumor) stem cells.

In one aspect, the dBHD and dBHD analog compositions of this invention are used to inhibit beta-catenin, a key protein in the Wnt-signaling path. While the invention is not limited by any particular mechanism of action, the compounds of this invention, including and dBHD-based compositions and dBHD analog compositions of the invention, can interfere in the accumulation of beta-catenin in the cell nucleus to inhibit the Wnt-signaling path at the transcriptional level.

In alternative embodiments, compounds of the invention (including dBHD-based compositions and dBHD analog compositions of the invention) comprise/consist of (are) compounds having a formula (a) as set forth in FIG. 5, wherein R₁ and/or the R₂ group are independently selected from the group consisting of hydrogen, halo, hydroxy (—OH), thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—NO₂), alkoxy, haloalkoxy, thioalkoxy, alkanoyl, haloalkanoyl and carbonyloxy; (b) the formula of (a), wherein the alkyl, haloalkyl, alkene, alkenyl in both or either of the R₁ and/or the R₂ groups is at least 1, 2, 3, 4, 5, 6, 7, 8, 9, 10, 11, 12, 13, 14, 15 or 16 or more carbons in length; (c) the formula of (a) or (b), wherein the heterocyclic moiety comprises a 5 membered ring or a 6 membered ring system; or (d) the formula of (c), wherein 5 membered ring system comprises an imidazole, thiazole, triazole or oxadiazole, or the 6 membered ring system comprises a pyridine, a pyrimidine or a pyrazine.

In one aspect, "alkenyl" and "alkynyl" groups are defined similarly to alkyl groups, and include straight-chain, branched-chain and cyclic monovalent hydrocarbyl radicals, and combinations of these, which contain only C and H when they are unsubstituted. However, alkenyl groups contain one or more carbon-carbon double bonds, and alkynyl groups contain one or more carbon-carbon triple bonds.

Typically, the alkyl, alkenyl and alkynyl substituents of the invention contain 1-8C (alkyl) or 2-8C (alkenyl or alkynyl). In alternative aspects, they contain 1-4C (alkyl) or 2-4C (alkenyl or alkynyl).

Alkyl, alkenyl and alkynyl groups are often substituted to the extent that such substitution makes sense chemically. In alternative aspects, substituents include, but are not limited to, halo, =O, —CN, —OR', —SR', —S(O)R', —SO₂R', —COOR', —C(O)NR'₂, —NR'₂ and —NHC(=NH)NH₂, where each R' independently represents H, C1-C4 alkyl or C5-C12 arylalkyl, or a heteroform of one of these.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue. When heteroatoms (typically N, O and S) are allowed to replace carbon atoms of an alkyl, alkenyl or alkynyl group, as in heteroalkyl groups, the numbers describing the group, though still written as, e.g., C1-C6, represent the sum of the number of carbon atoms in the group plus the number of such heteroatoms that are included as replacements for carbon atoms in the ring or chain being described. Such heteroalkyl groups may be optionally substituted with the same substituents as alkyl groups.

Where such groups contain N, the nitrogen atom may be present as NH or it may be substituted if the heteroalkyl or similar group is described as optionally substituted. Where such groups contain S, the sulfur atom may optionally be oxidized to SO or SO₂ unless otherwise indicated. For reasons of chemical stability, it is also understood that, unless otherwise specified, such groups do not include more than two contiguous heteroatoms as part of the heteroalkyl chain, although an oxo group may be present on N or S as in a nitro or sulfonyl group. Thus —C(O)NH₂ can be a C2 heteroalkyl group substituted with =O; and —SO₂NH— can be a C2 heteroalkylene, where S replaces one carbon, N replaces one carbon, and S is substituted with two =O groups.

While "alkyl" in one aspect includes cycloalkyl and cycloalkylalkyl groups, the term "cycloalkyl" may be used herein to specifically describe a carbocyclic non-aromatic group that is connected via a ring carbon atom, and "cycloalkylalkyl" may be used to describe a carbocyclic non-aromatic group that is connected to the base molecule through an alkyl linker. For example, cyclohexylalanine (Cha) comprises a cycloalkylalkyl substituent. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. Where an alkyl group is substituted with an aryl or heteroaryl group, it is referred to as an arylalkyl or heteroarylalkyl substituent.

In one aspect, an "aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like.

Any monocyclic or fused ring bicyclic system which has the characteristics of aromaticity in terms of electron distribution throughout the ring system is included in this definition. It also includes bicyclic groups where at least one ring has the characteristics of aromaticity, even though it may be fused to a nonaromatic ring. Typically, the ring systems contain 5-12 ring member atoms. In alternative aspects, the monocyclic heteroaryl groups contain 5-6 ring members, and the bicyclic heteroaryls contain 8-10 ring members.

Aryl and heteroaryl moieties may be substituted with a variety of substituents which are known in the art. In alternative aspects, substituents include, but are not limited to, halo, C1-C8 alkyl, —NO$_2$, —CN, —OR', —SR', —COOR', —C(O)NR'$_2$, and —NR'$_2$, where each R' independently represents H, C1-C4 alkyl or C5-C12 arylalkyl, or a heteroform of one of these.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moieties. "Heteroarylalkyl" refers to a moiety comprising an aryl group that is attached through a linking group, and differs from "arylalkyl" in that at least one ring atom of the aryl moiety or one atom in the linking group is a heteroatom selected from N, O and S.

An aryl or heteroaryl ring in an arylalkyl or heteroarylalkyl group may be optionally substituted on the aromatic portion with the same substituents described above for aryl groups. In alternative embodiments, an arylalkyl group includes a phenyl ring and a heteroarylalkyl group includes a C5-C6 monocyclic or C8-C10 fused bicyclic heteroaromatic ring, each of which may be optionally substituted with the groups defined above for aryl groups and a C1-C4 alkylene that is unsubstituted or is substituted with one or two C1-C4 alkyl groups, where the alkyl groups can optionally cyclize to form a ring, and wherein the alkyl or heteroalkyl groups may be optionally fluorinated. In certain embodiments, the arylalkyl or heteroarylalkyl ring comprises a phenol or an indole ring. In alternative aspects, substituents on phenyl include OH, C1-C4 alkoxy, and halo.

"Arylalkyl" and "heteroarylalkyl" groups are described by the total number of carbon atoms in the ring and alkylene or similar linker. Thus a benzyl group is a C7-arylalkyl group, and phenethyl is a C8-arylalkyl group.

"Alkylene" in one aspect refers to a divalent hydrocarbyl group; because it is divalent, it can link two other groups together. Typically it refers to —(CH$_2$)— where n is 1-8, or n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as —(CH$_2$)$_3$—, i.e., the specified length represents the number of atoms linking the attachment points rather than the total number of atoms in the hydrocarbyl group: —C(Me)$_2$- would thus be a one-atom linker, since the available valences are separated by only one atom. Where an alkylene group is substituted, the substituents include those typically present on alkyl groups as described herein, thus —C(=O)— is an example of a one-carbon substituted alkylene. Where it is described as unsaturated, the alkylene may contain one or more double or triple bonds.

"Heteroalkylene" in one aspect is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, —C(=O)NH— is an example of a two-carbon substituted heteroalkylene, where N replaces one carbon, and C is substituted with a =O group.

In one aspect, an "aminoalkyl" group refers to a C1-C6 alkyl group that is substituted with at least one amine group having the formula —NR2, where each R is independently H, C1-C8 alkyl, C5-C12 aryl and C5-C12 arylalkyl, or a heteroform of one of these. Such aminoalkyl groups may be optionally substituted on the alkyl portion with one or more other groups suitable as substituents for an alkyl group. In some embodiments, the aminoalkyl substituent is a 1-aminoalkyl group such as a 1-aminomethyl, 1-aminoethyl, 1-aminopropyl or 1-aminobutyl group. In certain embodiments, the aminoalkyl group may comprise a protected amine. One of skill in the art would appreciate that appropriate amine protecting groups may vary depending on the functionality present in the particular monomer. Suitably protected amines may include, for example, carbamates (e.g., tert-butoxycarbonyl, benzyloxycarbonyl, fluorenylmethyloxy-carbonyl, allyloxycarbonyl or (trialkylsilyl)ethoxycarbonyl), carboxamides (e.g., formyl, acyl or trifluoroacetyl), sulfonamides, phthalimides, Schiff base derivatives, and the like. In certain embodiments, an aminoalkyl group may be coupled through an alkylene or heteroalkylene linker to a group such as biotin, or a fluorophore-containing group, such as rhodamine, and such compounds may be useful for screening or mechanistic studies.

"Heteroform" in one aspect refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" in one aspect indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo", in one aspect includes fluoro, chloro, bromo and iodo. Fluoro and chloro can be used.

"Amino" in one aspect refers to $NR'_2$ wherein each R' is independently H, or is an alkyl, alkenyl, alkynyl, acyl, aryl, or arylalkyl group or a heteroform of one of these groups, as defined above, each of which may be optionally substituted with the substituents described herein as suitable for the corresponding type of group. In certain embodiments, the two R' groups on one nitrogen atom may be linked together to form an azacyclic ring.

In one aspect, an 'azacyclic' group refers to a heterocyclic group containing at least one nitrogen atom as a ring atom, wherein the group is attached to the base molecule through a nitrogen atom of the azacyclic group. Typically azacyclic groups are 3-8 membered monocyclic rings or 8-12 membered bicyclic fused ring systems, and may be saturated, unsaturated or aromatic and may contain a total of 1-3 heteroatoms independently selected from N, O and S as ring members. In certain embodiments, an azacyclic ring may comprise a nitrogen-containing ring fused to a phenyl ring. For example, the unnatural amino acid "Tic" comprises a tetrahydroisoquinoline ring, which represents a 10-membered fused bicyclic azacyclic group.

In alternative embodiments, the compositions of the invention, including the compounds of the invention (dBHD-based compositions and dBHD analog compositions of the invention), and the pharmaceutical compositions comprising them, and methods of the invention, are used to treat, prevent or ameliorate (including slowing the progression of) dysfunctional (e.g., abnormally proliferating) cells, such as cancer cells, or dysfunctional (e.g., abnormally proliferating) stem cells, including cancer or tumor stem cells.

In one aspect, the compounds of the invention (dBHD-based compositions and dBHD analog compositions of the invention) and methods of the invention inhibit the TCF/β-catenin (T Cell Factor/beta-catenin) transcription complex by disrupting the interaction between TCF and β-catenin proteins. In alternative embodiments, the invention provides method for inhibiting a β-catenin (beta-catenin) activity, comprising contacting a β-catenin with any compound of the invention, or the pharmaceutical composition of the invention, or the liposome of the invention, or the nanoparticle of the invention wherein optionally the contacting is in vitro, ex vivo or in vivo; or methods for interfering in the accumulation of beta-catenin in the cell nucleus to inhibit the Wnt-signaling path at the transcriptional level, comprising contacting a β-catenin with any compound of the invention, or the pharmaceutical composition of the invention, or the liposome of the invention, or the nanoparticle of the invention; wherein optionally the contacting is in vitro, ex vivo or in vivo.

In alternative embodiments, the compounds of the invention (dBHD-based compositions and dBHD analog compositions of the invention), and the pharmaceutical compositions comprising them, and methods, are used to stop, reverse or slow the growth and/or proliferation of dysfunctional (e.g., abnormally proliferating) stem cells, including cancer or tumor stem cells. While the invention is not limited by any specific mechanism of action, in one aspect, the compositions and methods of the invention are used to inhibit the Wnt-signal path downstream of the beta-catenin (β-catenin) decomposition complex; the normally functioning Wnt pathway are well known in the art; for example, the effects of inactivation of the signaling pathway when Wnt does not act on a target cell are well known in the art.

Thus, the compositions and methods of the invention can be used to disrupt the Wnt pathway—a series of events that occur when Wnt proteins bind to cell-surface receptors of the Frizzled family, causing the receptors to activate Dishevelled family proteins and ultimately resulting in a change in the amount of β-catenin that reaches the nucleus; Dishevelled (DSH) is a key component of a membrane-associated Wnt receptor complex which, when activated by Wnt binding, inhibits a second complex of proteins that includes axin, GSK-3, and the protein APC (or Adenomatosis Polyposis Coli, a human gene classified as a tumor suppressor gene). The axin/GSK-3/APC complex normally promotes the proteolytic degradation of the β-catenin intracellular signaling molecule. After this "β-catenin destruction complex" is inhibited, a pool of cytoplasmic β-catenin stabilizes, and some β-catenin is able to enter the nucleus and interact with TCF/LEF family transcription factors to promote specific gene expression. In one embodiment, the dBHD and analog compounds of the invention inhibit the TCF/β-catenin transcription complex by disrupting the interaction between TCF and β-catenin proteins.

The compositions and methods of the invention, including the pharmaceutical compositions of the invention, can be useful to treat, reverse, prevent (prophylaxis) or ameliorate any dysfunctional stem cell, or any abnormally (dysfunctional) dividing or metastasizing cancer cells or stem cells, e.g., a cancer stem cell or a tumor stem cell. Cancers that can be treated, prevented or ameliorated by using compositions and methods of this invention include lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and/or any combination thereof.

Also provided herein are kits comprising the compositions and methods of this invention, and instructions for making, formulating and/or using them, e.g., for the therapeutic and/or prophylactic applications as described herein.

The invention provides nanoparticles comprising any compound of this invention, or a compound made by any of the biosynthetic or synthetic methods of this invention.

The invention provides use of compounds of this invention for the manufacture of a medicament for the treatment, prevent or amelioration of diseases or conditions associated with dysfunctional stem cells, including cancer stem cells, including cancer stem cells associated with lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma or pituitary adenoma, and any combination thereof.

The invention also provides synthetic schemes (protocols) for synthesizing a compound, wherein the synthetic scheme comprises, or consists of, steps as described in FIG. 8, and the compound comprises a dibromohymenialdesine (dBHD), or (4Z)-4-(2-amino-5-oxo-3,5-dihydro-4H-imidazol-4-ylidene)-4,5,6,7-tetrahy-dropyrrolo(2,3-c)azepin-8(1H)-one, or analogs thereof.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

Like reference symbols in the various drawings indicate like elements.

DETAILED DESCRIPTION

Figure 5:
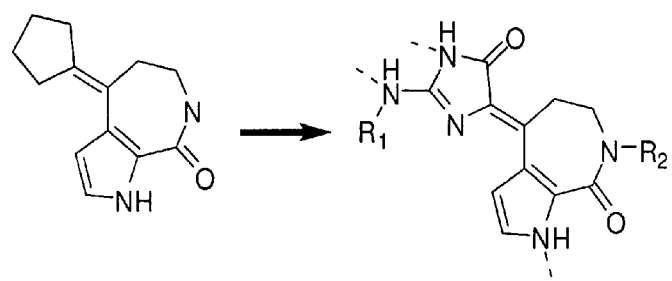
FIG. 5 illustrates the exemplary formula for a genus of compounds of the invention, these compounds based on a basic pyrroloazepine scaffold, with the alternative substituent groups R1 and R2 described herein.

The invention provides compositions comprising debromohymenialdesine (dBHD) (see compound I, FIG. 1) analogs—the compounds of the invention (dBHD analogs of the invention) as illustrated in FIG. 5, and pharmaceutical compositions comprising them, and methods for inhibiting cancer (tumor) stem cell growth, but not normal stem cell growth. In alternative embodiments, the compositions and methods of the invention, including the dBHD analogs of the invention, and the pharmaceutical compositions comprising them, are used to treat, prevent or ameliorate (including slowing the progression of) a cancer, e.g., a prostate or a leukemia.

In alternative embodiments, the dBHD and dBHD analog compositions of this invention inhibit beta-catenin of the Wnt-signaling path. While the invention is not limited by any particular mechanism of action, the compounds of this invention, including and dBHD and analogs, slow or prevent the accumulation of beta-catenin in a cell nucleus, thus modifying (e.g., inhibiting) the Wnt-signaling pathway at the transcriptional level.

A drug screening of secondary metabolites from marine sponges identified pyrroloazepines which inhibit beta-catenin in HEK293 cells transfected with TCF/LEF-dependent reporter genes in the low micromolar range. Structure-activity profiling within this family of compounds conferred specific structural requirement for inhibition and identified a compound, MC-001. Significantly MC-001, in toxicity tests in BALB/C mice showed no adverse affects in these animals even at doses of 100 mg/kg.

Pharmaceutical Compositions

The invention provides dBHD and dBHD-based compositions as described herein, including pharmaceutical compositions, e.g., in the manufacture of medicaments for inhibiting the growth of non-normal stem cells, e.g., cancer stem cells.

In alternative embodiments, the dBHD-based compositions and dBHD analogs of the invention are formulated with a pharmaceutically acceptable carrier. In alternative embodiments, the pharmaceutical compositions of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton Pa. ("Remington's").

Therapeutic agents of the invention can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the dBHD-based compositions and dBHD analogs of the invention include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with non-toxic pharmaceutically acceptable excipients which are suitable for manufacture. Formulations may comprise one or more diluents, emulsifiers, preservatives, buffers, excipients, etc., and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a chimeric polypeptide or peptidomimetic of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration of the hydrophobic active agents of the invention, including dBHD-based compositions and dBHD analog compositions of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) *J. Pharmacol. Exp. Ther.* 281:93-102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In practicing this invention, the pharmaceutical compounds can also be administered by in intranasal, intraocular and intravaginal routes including suppositories, insufflation, powders and aerosol formulations (for examples of steroid inhalants, see Rohatagi (1995) *J. Clin. Pharmacol.* 35:1187-1193; Tjwa (1995) *Ann. Allergy Asthma Immunol.* 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols.

In practicing this invention, the pharmaceutical compounds can also be delivered as microspheres for slow release in the body. For example, microspheres can be administered via intradermal injection of drug which slowly release subcutaneously; see Rao (1995) *J. Biomater Sci. Polym. Ed.* 7:623-645; as biodegradable and injectable gel formulations, see, e.g., Gao (1995) *Pharm. Res.* 12:857-863 (1995); or, as microspheres for oral administration, see, e.g., Eyles (1997) *J. Pharm. Pharmacol.* 49:669-674.

In practicing this invention, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. No. 20040028670.

The compositions and formulations of the invention can be delivered by the use of liposomes (see also discussion, below). By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) *J. Microencapsul.* 13:293-306; Chonn (1995) *Curr. Opin. Biotechnol.* 6:698-708; Ostro (1989) *Am. J. Hosp. Pharm.* 46:1576-1587.

The formulations of the invention can be administered for prophylactic and/or therapeutic treatments. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). For example, in alternative embodiments, pharmaceutical compositions of the invention are administered in an amount sufficient to treat, prevent and/or ameliorate normal, dysfunction (e.g., abnormally proliferating) blood vessels, including endothelial and/or capillary cell growth; including neovasculature related to (within, providing a blood supply to) hyperplastic tissue, a granuloma or a tumor. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of dBHD-based compositions and dBHD analog compositions of the invention in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for treating cancer, septic shock, infection, fever, pain and related symptoms or conditions. For example, the methods and/or compositions and formulations of the invention can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Nanoparticles and Liposomes

The invention also provides nanoparticles and liposomal membranes comprising compounds of this invention which target specific molecules, including biologic molecules, such as polypeptide, including cell surface polypeptides. Thus, in alternative embodiments, the invention provides nanoparticles and liposomal membranes targeting diseased and/or tumor (cancer) stem cells and dysfunctional stem cells.

In alternative embodiments, the invention provides nanoparticles and liposomal membranes comprising (in addition to comprising compounds of this invention) molecules, e.g., peptides or antibodies, that selectively target diseased, infected, dysfunctional and/or cancer (tumor) cell receptors. In alternative embodiments, the invention provides nanoparticles and liposomal membranes using IL-11 receptor and/or the GRP78 receptor to targeted receptors on cells, e.g., on tumor cells, e.g., on prostate or ovarian cancer cells. See, e.g., U.S. patent application publication No. 20060239968.

Thus, in one aspect, the compositions of the invention are specifically targeted for inhibiting, ameliorating and/or preventing endothelial cell migration and for inhibiting angiogenesis, e.g., tumor-associated or disease- or infection-associated neovasculature.

The invention also provides nanocells to allow the sequential delivery of two different therapeutic agents with different modes of action or different pharmacokinetics, at least one of which comprises a composition of this invention. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients suffering from a diseases or condition as described herein, e.g., such as cancer, inflammatory diseases such as asthma, autoimmune diseases such as rheumatoid arthritis or infectious diseases. In treating cancer, a traditional antineoplastic agent is contained in the outer lipid vesicle of the nanocell, and an antiangiogenic agent of this invention is loaded into the nanocore. This arrangement allows the antineoplastic agent to be released first and delivered to the tumor before the tumor's blood supply is cut off by the composition of this invention.

The invention also provides multilayered liposomes comprising compounds of this invention, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome of the invention may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavanoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

The invention also provides nanoparticles comprising compounds of this invention to deliver a composition of the invention as a drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

Liposomes

The compositions and formulations of the invention can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) *J. Microencapsul.* 13:293-306; Chonn (1995) *Curr. Opin. Biotechnol.* 6:698-708; Ostro (1989) *Am. J. Hosp. Pharm.* 46:1576-1587. For example, in one embodiment, compositions and formulations of the invention are delivered by the use of liposomes having rigid lipids having head groups and hydrophobic tails, e.g., as using a polyethyleneglycol-linked lipid having a side chain matching at least a portion the lipid, as described e.g., in US Pat App Pub No. 20080089928. In another embodiment, compositions and formulations of the invention are delivered by the use of amphoteric liposomes comprising a mixture of lipids, e.g., a mixture comprising a cationic amphiphile, an anionic amphiphile and/or neutral amphiphiles, as described e.g., in US Pat App Pub No. 20080088046, or 20080031937. In another embodiment, compositions and formulations of the invention are delivered by the use of liposomes comprising a polyalkylene glycol moiety bonded through a thioether group and an antibody also bonded through a thioether group to the liposome, as described e.g., in US Pat App Pub No. 20080014255. In another embodiment, compositions and formulations of the invention are delivered by the use of liposomes comprising glycerides, glycerophospholipides, glycerophosphinolipids, glycerophosphonolipids, sulfolipids, sphingolipids, phospholipids, isoprenolides, steroids, stearines, sterols and/or carbohydrate containing lipids, as described e.g., in US Pat App Pub No. 20070148220.

Therapeutically Effective Amount and Dose

The formulations of the invention can be administered for prophylactic and/or therapeutic treatments; for example, the invention provides methods for treating, preventing or ameliorating a disease or condition associated with dysfunctional stem cells or cancer stem cells comprising use of the compound of the invention. In therapeutic applications, compositions are administered to a subject already suffering from a condition, infection or disease in an amount sufficient to cure, alleviate or partially arrest the clinical manifestations of the condition, infection or disease (e.g., disease or condition associated with dysfunctional stem cells or cancer stem cells) and its complications (a "therapeutically effective amount"). In the methods of the invention, a pharmaceutical composition is administered in an amount sufficient to treat (e.g., ameliorate) or prevent a disease or condition associated with dysfunctional stem cells or cancer stem cells. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat the treat (e.g., ameliorate) or prevent asthma and/or its symptoms. For example, an exemplary pharmaceutical formulation for oral administration of an ITK-inhibitory nucleic acid or polypeptide of the invention is in a daily amount of between about 0.1 to 0.5 to about 20, 50, 100 or 1000 or more µg per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The compositions and formulations of the invention can further comprise other drugs or pharmaceuticals, e.g., compositions for treating disease or condition associated with dysfunctional stem cells or cancer stem cells, and related conditions. The methods of the invention can further comprise co-administration with other drugs or pharmaceuticals, e.g., compositions for treating cancer or related conditions. For example, the methods and/or compositions and formulations of the invention can be co-formulated with and/or co-administered with analgesics (e.g., pain killers), antibiotics, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Kits and Libraries

The invention provides kits comprising compositions of this invention and methods of the invention, including cells and/or fish of the invention, target sequences, transfecting agents, transducing agents, instructions (regarding the methods of the invention), or any combination thereof. As such, kits, cells, vectors and the like are provided herein.

The invention will be further described with reference to the following examples; however, it is to be understood that the invention is not limited to such examples.

EXAMPLES

Example 1

The invention provides compositions comprising debromohymenialdesine (dBHD) and dBHD analogs, and pharmaceutical compositions comprising them, and methods for inhibiting cancer cells, including cancer (tumor) stem cell growth, but not normal stem cell growth. This example describes methods and animal models for demonstrating the efficacy of compounds of the invention, and described data demonstrating the efficacy of compounds of the invention.

In a drug screening effort using natural products isolated from the marine environment, we have discovered pyrrolo-pazepine molecules, isolated from marine sponges, which inhibit the Wnt/β-catenin pathway. These pyrrolo-pazepine compounds of the invention inhibit a TCF/LEF dependent reporter gene in HEK293 cells in the low micromolar range. Structure-activity profiling identified specific structural requirements for inhibition. When tested in leukemia cancer stem cells, debromohymenialdesine (dBHD) and analogs completely abrogated self-renewal of the stem cells at 2 uM drug concentrations; inhibition of wnt/b-catenin signaling was confirmed. While the invention is not limited by any particular mechanism of action, computer modeling suggests that dBHD may inhibit the TCF/β-catenin transcription complex by disrupting the interaction between TCF and β-catenin proteins.

We have produced this compound by total synthesis and confirmed its activity in the cell based reporter system described above. In addition, we have demonstrated that this compound is well tolerated in mice. Injections of up to 100 mg/kg showed no toxic effects.

1.) Synthesis of natural compound and analogs from the natural scaffold. We have devised a synthetic strategy for the total synthesis of the natural compound in high yield and via intermediate compounds.

2.) Cell based screening of the pyrrolo-azepine lead and analogs. Inhibition of the TCF/beta-catenin transcription complex can be tested using the HEK293 cell based reporter system, and using prostate tumor cell lines PC3, and DU145 and LNCaP.

3.) In vivo studies. The results of the cell based screens can be used to select compounds for in vivo testing. Efficacy of these novel compounds of the invention can be demonstrated in a PC3 orthotopic human prostate cancer mouse model. This cell line is known to produce Wnt proteins, which act in a paracrine fashion to induce osteoblastic activity in bone metastases. This system can be used to demonstrate that the compounds inhibit the growth of the primary tumors and metastatic lesions.

Figure 1:
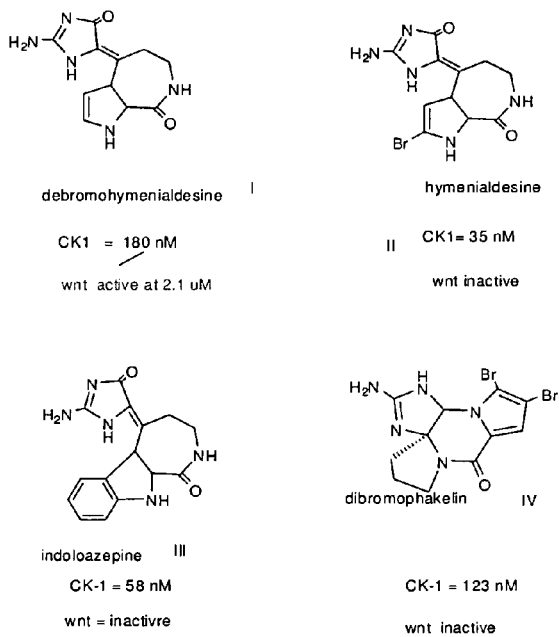
FIG. 1 illustrates exemplary compounds that can be used in pharmaceutical compounds of this invention, including debromohymenialdesine (I), hymenialdesine (II) and indoloazepine (III) and dibromophakelin (IV).
Figure 2:
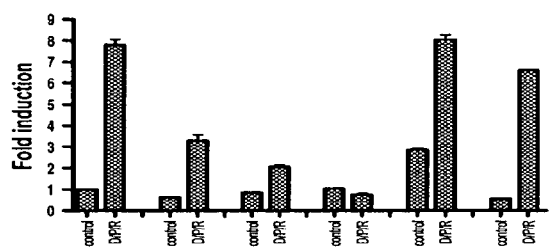
FIG. 2 in graphic form illustrates data comparing inhibition of beta-catenin in a "Top-flash assay", as described in detail in Example 1, below.

A summary of fine tuning structure-activity-relationships for structurally related pyrroloazepines is shown in FIGS. 1 and 2. The results show that these compounds inhibit CK1 (and other kinases, data not shown) at comparable levels of potency. However, only the debromohymenialdesine (dBHD) compound (designated "MC-001") inhibited wnt-signaling in HEK293 cells transfected with a TCF/LEF dependent reporter gene. Hymenialdesine (II) and indoloazepine (III) and dibromophakelin (IV) (see FIG. 1) all of which are structurally closely related to MC-001 (dBHD) did not inhibit this path even at concentrations of 50 uM. The major difference between debromohymenialdesine ("MC-001", or dBHD) and the three other structures is the absence of substituents in the pyrrolo portion of the molecules. In one aspect, the important triad of amino hydrogens must be unobstructed for high affinity binding. These observations are useful for the design of novel inhibitors based on the pyrroloazepine scaffold. In one embodiment, the invention provides compounds comprising the pyrroloazepine scaffold having the requisite triad of amino hydrogens.

FIG. 2 in graphic form illustrates data comparing inhibition of beta-catenin in a "Top-flash assay." In this assay HEK 293 cells were transfected with a TCF/LEF dependent reporter gene and expression plasmid for Dsh. After overnight incubation, the cells were treated with the indicated amounts of debromohymenialdesine ("MC-001", or dBHD, or dbHD), which is compound I in FIG. 1, analog II and III, or vehicle alone, after which the reporter gene activity was measured. All cells were also transfected with a reporter gene control for testing the transfection efficiency. In FIG. 2, the first pair of bars (to the left, closest to the y, or "fold induction", axis) is DMSO, then moving right, the second pair of bars is 5 µM debromohymenialdesine, or dbHD (compound I of FIG. 1), then 10 µM dbHD, then 20 µM dbHD, then 50 µM compound II of FIG. 1, then 50 µM compound III of FIG. 1.

Figure 3:
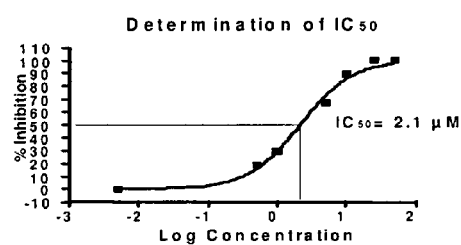
FIG. 3 in graphic form illustrates a dose response curve for dibromohymenialdesine from a cell line assay, as described in detail in Example 1, below.

A dose response curve for debromohymenialdesine, or "MC-001", or dbHD (or dBHD), (compound I of FIG. 1) from the HEK293 cell line assay is shown in FIG. 3. The curve is well behaved showing a relatively steep sigmoidal inhibition-concentration profile with an $IC_{50}$ value of 2 uM.

We determined some physical properties of debromohymenialdesine, or "MC-001", or dbHD (or dBHD), (compound I of FIG. 1):

Solubility in water 0.022 mg/ml
log P: −0.58
Molecular weight: 245
Storage stability: several months at RT Debromohymenialdesine, or MC-001 showed a log P (i.e., partition coefficient) of −0.58 indicating a relatively low lipophilicity. Thus, modification of this compound by incorporating hydrophobic groups will be of benefit to increase cell membrane permeability.

Figure 4:
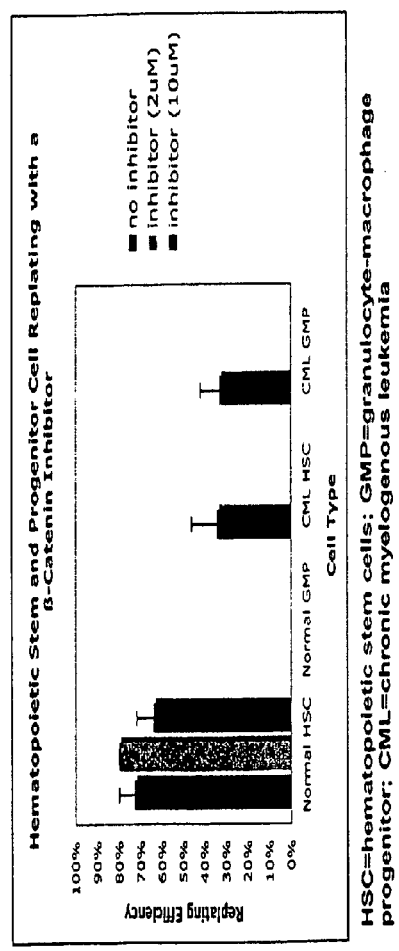
FIG. 4 illustrates data in graphic form showing chronic myelogenous leukemia stem cell inhibition with debromohymenialdesine, as described in detail in Example 1, below.

FIG. 4 illustrates data in graphic form showing chronic myelogenous leukemia stem cell inhibition with debromohymenialdesine, or "MC-001", or dbHD (or dBHD), (compound I of FIG. 1).

To assess the effects of debromohymenialdesine, or "MC-001", or dbHD (or dBHD) on wnt/beta-catenin induced self-renewal, hematopoietic stem cells (HSC), GMP and lineage positive cells from normal and advanced phase CML, peripheral blood and marrow were clone sorted with and without Wnt inhibitors, including recombinant Dkk1, lentiviral axin and debromohymenialdesine ("MC-001", or dbHD, or dBHD).

On day 10, individual colonies were plucked and replicated in new methylcellulose and the replating efficiency was determined. The results are shown in FIG. 4. Recombinant Dkk1 did not inhibit CML/HSC while lentiviral axin and debromohymenialdesine ("MC-001", or dbHD, or dBHD) inhibited both HSC and GMP at doses that spared normal HSC replating. The results in FIG. 4 demonstrate that MC-001 completely abrogates replating efficiency at concentrations as low as 2 uM.

In vivo inhibition of LSC self-renewal with this dBHD inhibitor can also be demonstrated in a bioluminescent imaging model.

We synthesized dBHD as previously described by Portevin, et al., (2003) "An expedious multigram preparation of the marine protein kinase inhibitor debromohymenialdisine," *Tetrahedron letters* 44:9263-9265, but with modifications of this procedure for obtaining material with improved yield, see Example 3, below. The synthetically obtained compound showed activity comparable to the natural product and can be up-scaled to gram quantities to allow for biological testing.

The invention provides compounds (including pharmaceutical compositions) based on a basic pyrroloazepine scaffold as illustrated in FIG. 5; the alternative embodiments (alternative species) of the groups R1 and R2 in the generic compound of FIG. 5, as described herein, lend diversity to impart potency, selectivity and drug-likeness.

In alternative embodiments, the triad hydrogen bonds donating motive (dotted lines) of the amino groups on the left side of the molecule are retained; avoiding stereo-blocking substituents in the pyrrozole ring. The compounds of the invention, as drug-like heterocycles, overcome potential liabilities of the natural compound dBHD, such as its relative low partition coefficient (log P) which could limit membrane permeability, and bioavailability and potential metabolic stability issues.

The compounds of the invention can comprise any 5 membered ring, including e.g., diazoles, triazole, oxadiazoles and any 6 membered rings, including e.g., pyridines, pyrimidines and pyrazines.

In addition to heterocycle substitution, the compounds of the invention comprise the basic pyrroloazepine scaffold by substitution reactions with lipophilic R groups, e.g., where R1 and R2 comprise any lipophilic R group, including hydrophobic short aliphatic chains and aromatic groups.

Improvements in the relative low aqueous solubility of the natural compound dBHD are realized by modifications in the R substituents, including pyperazino and morpholino or ethylene oxide moieties. The effectiveness of these modifications on the basic pyrrolo-azepine scaffold can be assessed in cell based wnt/b-catenin inhibitions screens.

In one embodiment, the invention provides for a reaction scheme for the synthesis of Wnt-signaling path inhibitors of the invention based on the total synthesis of the natural compound dBHD, as illustrated in the synthesis schematic of FIG.

6: where modifications of the azepine ring amide structure to introduce the R2 moiety are carried out as post reaction modification of structure VI. Potentially this modification could result in some side-side reactions affecting yields.

Alternatively, the invention provides a substitution reaction of the amide nitrogen in compound III to introduce the R1 group. Heterocyclic moieties for substitution reactions include but are not be limited to 5 membered rings including imidazoles, thiazoles, triazoles and oxadiazoles, and 6 membered ring systems including pyridines, pyrimidines and pyrazines. The proposed synthetic effort can be guided by computational modeling of analogs using the MOLSOFT™ (La Jolla, Calif.) modeling program software and published structural data of Tcf/b-catenin interactions Inhibition of biological markers of Tcf4/beta-catenin transactivation: initial screening of inhibition of the wnt/b-catenin path can be done in the established HEK 293 cell line assay. This screen can be a guide for a synthetic effort and can provide initial structure-activity profiles. Compounds with highest potency can be screened in prostate cancer cell lines. These cell lines can be transfected with constructs of TOP-Flash, containing 3 Tcf consensus binding sites upstream of firefly luciferase DNA, a plasmid with mutated binding sites. Transfected cells can be incubated with various concentrations of selected compounds. After 24 hr, cells can be lysed in luciferase cell culture lysis buffer and incubated with beta-gal assay buffer and reporter lysis buffer for 2 hr, and $A_{420}$ can be measured in a microplate spectrophotometer to determine beta-galactosidase activity. Results can be expressed as the means of normalized ratios for each triplicate set. Reporter activity in compound-treated cells can be expressed as the percentage of vehicle treated samples.

Screening of the Tcf/beta-catenin complex: the interaction between Tcf factors and beta-catenin requires a minimal N-terminal Tcf fragment and the central domain of 12 armadillo repeats in beta-catenin. The established procedure described, e.g., by Lepourcelet, et al. (2004) "Small-molecule antagonists of the oncogenic Tcf/beta-catenin protein complex," *Cancer Cell* 5:91-102, based on a 96 well plate ELISA assay is employed, with an AP conjugated anti-GST-antibody to register the disruption of the Tcf/beta-catenin complex by the reduction of AP values relative to the background. Enzyme activity can be assessed in a fluorescent plate reader using fluorescent AP substrate ATTOPHOS™ (JBL Scientific). Compound effects can be expressed as the concentration required to inhibit 50% of GST-Tcf binding to beta-catenin-coated wells.

Cell based assays: Protein extracts from the PC3 prostate cancer cell line with compounds identified as active in the ELISA screen can be assessed by SDS-PAGE and immunoblotting to confirm the disruption of the Tcf-beta-catenin complex and with other proteins in the cell extracts. Inhibition of interaction of selected compounds with GST-Tcf-4 can be determined in a dose dependent manner and compared to a vehicle control.

Figures 7A, 7B:
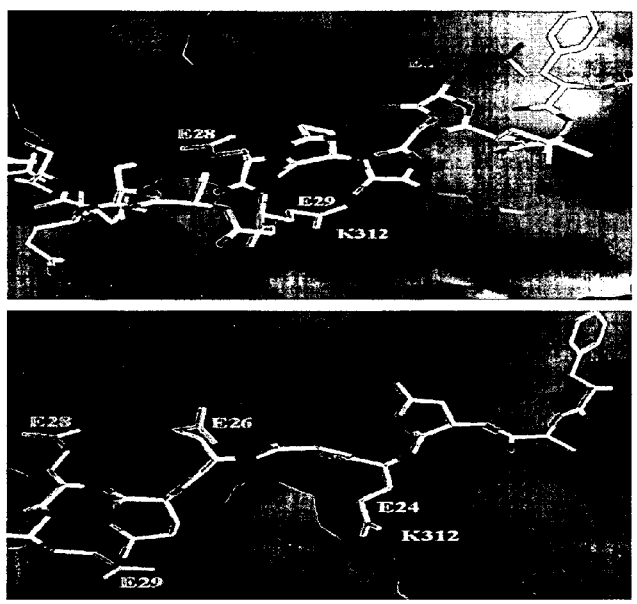
FIG. 7: illustrates a Tcf/beta-catenin complex and a binding mode of dibromohymenialdesine; comparison of the structural conformations of Tcf4 and Tcf3 near the Lysine 312 (hot spot): stick models of FIG. 7(a) (top) Tcf4 and FIG. 7(b) (bottom) Tcf3 on top of beta-catenin molecular surface, which has been shaded in blue for basic and read for acidic regions.
FIG. 7(c) illustrates a bonding diagram of the Tcf4 helical region.
FIG. 7(d) illustrates a computational modeling of a pyrroloazepine, as described e.g., in Example 1, below.
Figure 7C:
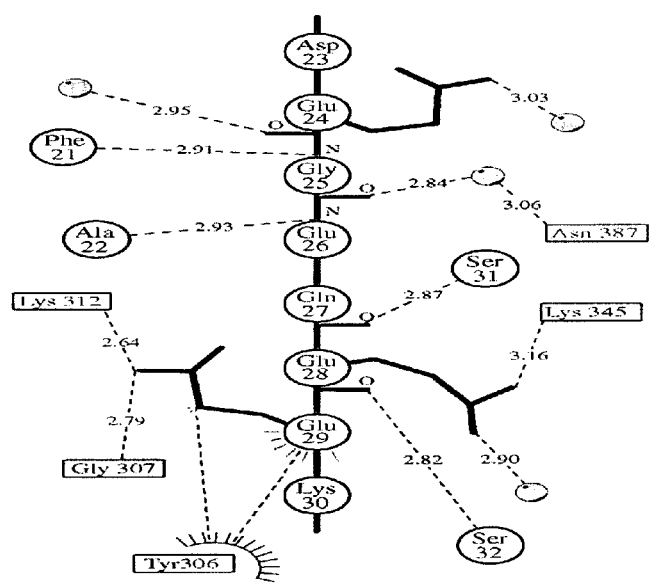
Figure 7D:
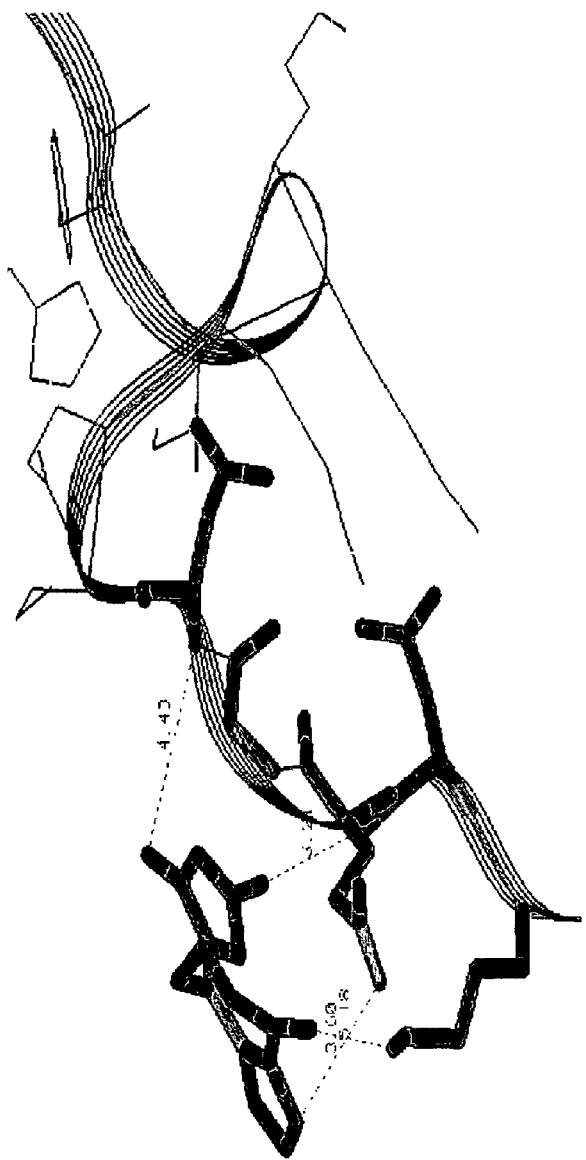

Computational Modeling:

Computational modeling of a pyrroloazepine, e.g., as illustrated in FIG. 7(d) illustrates a possible binding site at the Tcf-4-beta-catenin interface. Computational modeling defines a hot spot which can be exploited for structure-guided drug design. This region is investigated using the basic natural product dBHD scaffold as a staring point for virtual screening.

Starting with the published crystal structure of the Tcf/catenin complex (see, e.g., Graham, et al. (2001) "Tcf4 can specifically recognize beta-catenin using alternative conformations, *Nature Structural Biology* 8(12):1048-1052) a binding mode wherein the inhibitor competes with β-catenin for TcF4 in the kinked helical region as shown in FIG. 7(d) can be probed for debromohymenialdesine ("MC-001", or dbHD, or dBHD) and various analogs. The interactions shown in FIG. 7(d) can be refined to resolve all near neighbor interactions and use this information in subsequent energy filtering and visual inspection of binding modes for novel analog structures. Several selection criteria can be used: association energy, contact energy, intramolecular ligand strain, Van der Walls repulsion and visual inspection. Subsets of compounds can be scored for the above parameters. These scores when combined with other selection criteria, such as the Lipinsky rule of 5 and other drugability parameters such as polar surface area and number of rotatable bonds can be the basis for reiteration of structure-activity profiles. The results from these virtual screening studies can aid in drug design efforts in verification of the disruption of Tcf/beta-catenin complexes from this experimental data.

In FIG. 7: Tcf/beta-catenin complex and binding mode of dibromo-hymenialdesine ("MC-001", or dbHD, or dBHD); comparison of the structural conformations of Tcf4 and Tcf3 near the Lysine 312 (hot spot): stick models of FIG. 7(a) (top) Tcf4 and FIG. 7(b) (bottom) Tcf3 on top of beta-catenin molecular surface, which has been shaded in blue for basic and read for acidic regions. FIG. 7(c): bonding diagram of the Tcf4 helical region. The Tcf4 residues are shown in black and beta-catenin residues in red. Hydrophobic interactions are denoted by red starburst and hydrogen bonding interaction in green.

Prostate Tumor Cell Proliferation Assays: three cell lines PC3, DU145 and LNCap, can be used in cell proliferation assays using XTT as a vital stain. $10^4$ cells/well in 96 well plates can be incubated under standard cell culture conditions for 24 hr and selected compounds can be added at concentrations ranging from 100 uM to 10 picomolar. After 72 hr XTT dye can be added and the plates can be read periodically until the absorbance at 450 nm will reach a value of about 1.5 for the vehicle controls. The absorbance-concentration profiles can be constructed from the averages of duplicate determination and the concentration of 50% inhibition of cell growth can be calculated from these curves.

Validation of inhibitor activity in vivo: in one embodiment, an art-recognized animal model for cancer, in particular, for prostate cancer, comprising an orthotopic xenograft mouse prostate tumor model, is employed for bioluminescence screening to validate (demonstrate) the in vivo activity of the most potent analog selected from the cell based assays. Briefly, in athymic male nude mice (nu/nu; 6-8 weeks of age) obtained from Harlan Sprague Dawley, after total body anesthesia with AVERTIN™ (tribromoethanol), a low midline incision can be made in the lower abdomen. A suspension of $10^6$ tumor cells in 20 uL of PBS can be injected into the lateral lobe of the prostate, and the wound can be closed. This concentration of cells can be needed to consistently achieve tumor growth within 7 days of implantation. At day 7, 9, 11 and 14, a Wnt inhibitor, e.g., a composition of this invention, can be injected IP with vehicle as a control using 6 to 8 animals per experimental variable.

The dosage of administration can be determined according to the results from MTD and half lives assays. Primary tumor growth and metastases can be imaged daily by using the IVIS-100 bioluminescence system. The tumor weight also can be measured when the animals are terminated. Statistical comparison can be performed using analysis of variance for significance between different values using GRAPHPAD-PRISM™ (GraphPadPrism™) software (GRAPHPAD™ software, San Diego Calif.). Values can be expressed as mean S.D. from at least three separate experiments, and differences can be considered significant at p value of less than 0.05.

Example 2

The invention provides pharmaceutical compositions comprising dibromohymenialdesine (dBHD) and dBHD analogs, and methods for inhibiting cancer cells and dysfunctional stem cells, including compositions and methods for inhibiting cancer (tumor) stem cell growth.

The debromohymenialdisine-based compounds of this invention, and pharmaceutical formulations comprising them, used to practice this invention can be made (e.g., using synthetic and/or biosynthetic systems), formulated (e.g., a pharmaceutical compositions, e.g., in varying dosages) by incorporating all or part of any known formulation and/or method, for example:

U.S. Pat. No. 7,193,079, to Tepe, describing the preparation of hymenialdisine derivatives;

U.S. Pat. No. 5,565,448, Nambi, et al., describing medicants which contain hymenialdisine or debromohymenialdisine, used to inhibit protein kinase C;

U.S. Pat. No. 5,616,577, Nambi, et al., describing methods using hymenialdisine or debromohymenialdisine to inhibit protein kinase C;

U.S. Pat. No. 5,591,740, Chipman, et al., describing using compositions comprising hymenialdisine or debromohymenialdisine to treat osteoarthritis;

U.S. Pat. No. 5,621,099, Annoura, et al., describing a method for synthesizing hymenialdisine, bromohymenialdisine, and related compounds;

U.S. Pat. Nos. 5,834,609, 6,103,899, and 6,218,549, and U.S. patent publication no. 20010012891, all to Horne, et al., describing bicyclic aminoimidizole compounds;

U.S. Pat. Nos. 6,197,954; 6,211,361; 6,528,646; published U.S. Patent Application No. 2001/0012891 A1, all to Horne, et al., describing processes for synthesizing hymenialdisine, related compounds, and their intermediates;

U.S. Patent Application publication serial number 20030060457 A1 to Schaffer, et al., describing hymenialdisine as a cdk inhibitor which can be used as an inhibitor of gene expression, replication, and reactivation in pathogenic agents;

EP1106180A1 and WO 0141768 A2, to Meijer, describing using hymenialdisine and related compounds such as debromohymenialdisine to inhibit cyclin dependent kinases, GSK-3 beta, and casein kinase 1;

U.S. Patent Application publication serial numbers 20070060594 (describing methods of preparing pyridinyl acetonitriles); 20070049575 (describing synthesis and biological activity of indoloazepines and acid amine salts thereof which are structurally related to naturally-occurring hymenialdisine); 20060293305, 20060287296, 20060276451 and 20040235820 (describing indoloazepines to inhibit kinases CHK1 and CHK2); 20060024691 (describing activation of a steroid nuclear receptor); 20040209799 (describing methods for treating osteoarthritis using hymenialdisine, debromohymenialdisine and variants and derivatives); 20030105075 (describing using hymenialdisine or derivatives).

Example 3

The invention provides pharmaceutical compositions comprising dibromohymenialdesine (dBHD),

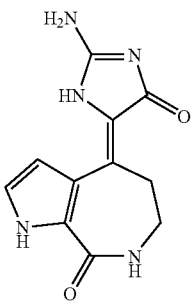

I and dBHD analogs, e.g., as described herein, and methods for making and using them. The invention also provides compositions and pharmaceutical compositions comprising as set forth in FIG. 5, for example:

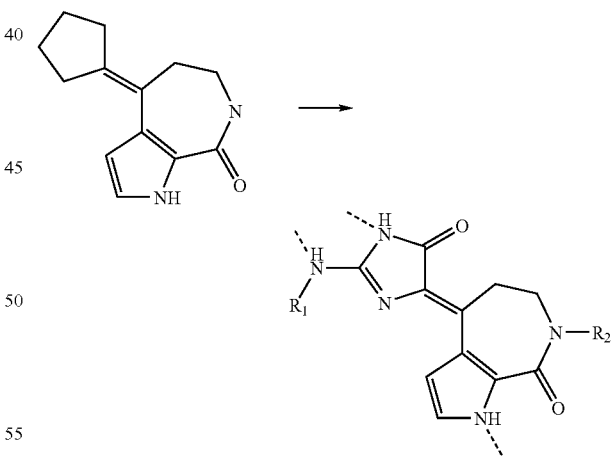

wherein $R_1$ and/or the $R_2$ group are independently selected from the group consisting of hydrogen, halo, hydroxy (—OH), thiol (—SH), cyano (—CN), formyl (—CHO), alkyl, heteroalkyl, heteroalkenyl, heteroalkynyl, haloalkyl, alkene, alkenyl, alkynyl, aryl, substituted aryl, amino, nitro (—NO$_2$), alkoxy, haloalkoxy, thioalkoxy, alkanoyl, haloalkanoyl and carbonyloxy.

Figure 6:
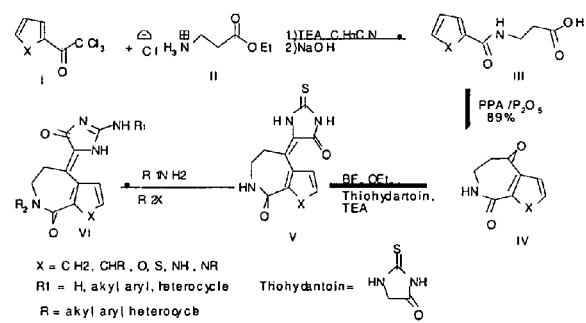
FIG. 6 illustrates a reaction scheme of the invention for the synthesis of Wnt-signaling path inhibitors of the invention, this synthetic scheme based on the total synthesis of the natural compound dBHD, as described in detail, below.

An exemplary protocol for synthesizing this or any other dibromohymenialdesine (dBHD)-based or dBHD analog compound of this invention is illustrated in FIG. 6:

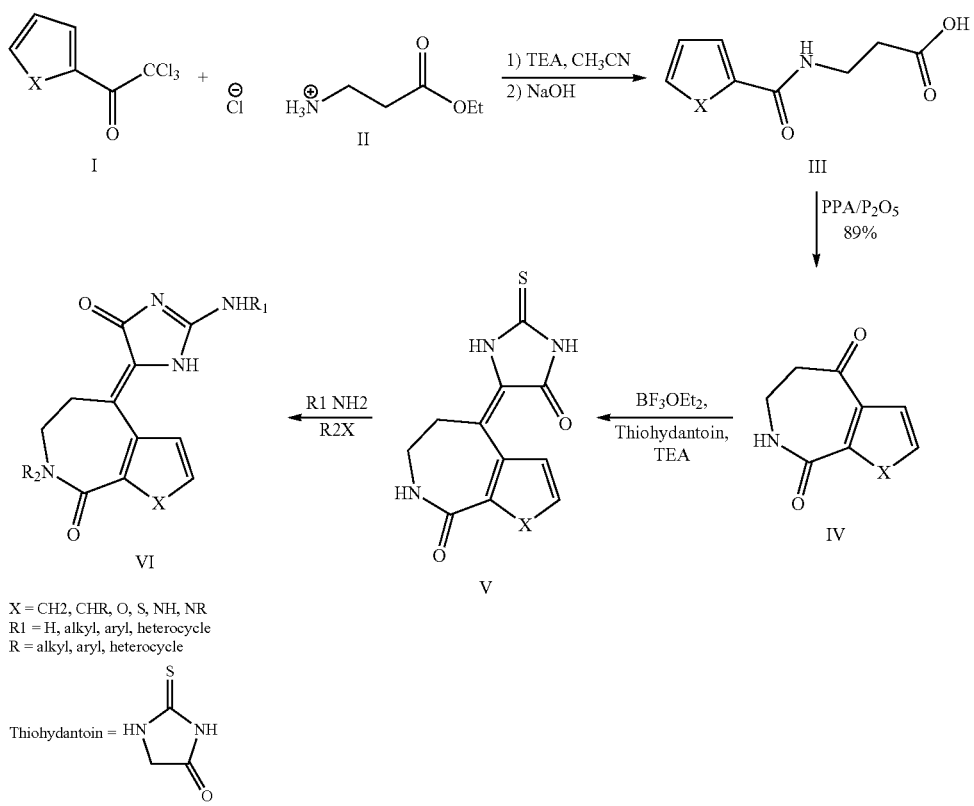

X = CH2, CHR, O, S, NH, NR
R1 = H, alkyl, aryl, heterocycle
R = alkyl, aryl, heterocycle

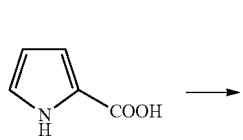

Figure 8:
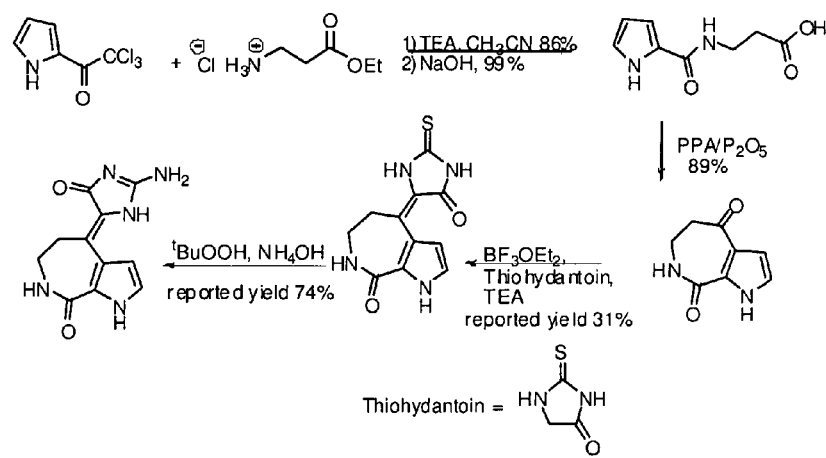
FIG. 8 illustrates a synthetic scheme of the invention, an exemplary method for making dibromohymenialdesine (dBHD)-based or dBHD analog compounds of this invention, as described e.g., in Example 3, below.

An exemplary protocol for synthesizing this or any other dibromohymenialdesine (dBHD)-based or dBHD analog compound of this invention is illustrated in FIG. 8.

The dibromohymenialdesine (dBHD) used to practice this invention can be synthesized by any scheme known in the art, e.g., the synthesis scheme as described by Annoura and Tatsuoka (H. Annoura, T. Tatsuoka; *Tetrahedron Lett.*; Vol. 36, (1995), pp. 413-416), which relies on the preparation of aldisine 2 in three steps starting from 2-pyrrole carboxylic acid (Scheme 1):

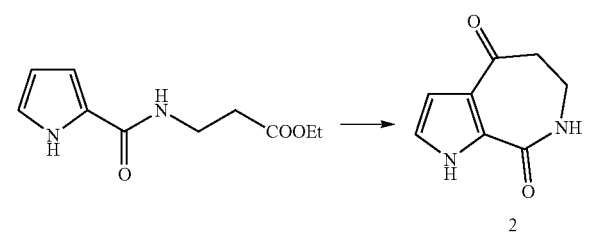

After protection of the two nitrogen atoms of 2, the imidazolone ring can be introduced by the preparation of an [alpha]-mesyloxy ester, which further reacts with guanidine to give 1.

Another known synthesis that can be used to make dibromohymenialdesine (dBHD) used to practice this invention is published by (Y. Xu, K. Yakushijin, D. A. Horne; *J. Org. Chem.*; Vol. 62, (1997), pp. 456-464), where the pyrroloazepinone 4 is obtained from dioxolane 3, itself prepared from pyrrole in 4 steps (Scheme 2).

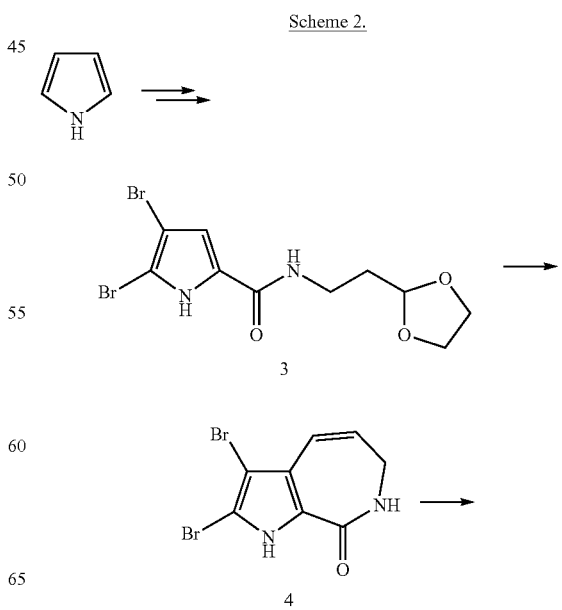

27

-continued

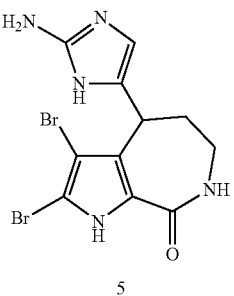

5

The aminoimidazole present in hymenine 5 can then be converted by oxidative bromination to an imidazolinone ring. DBH can finally be obtained after hydrogenolysis of the bromine atoms on the pyrrole ring.

Another known synthesis that can be used to make dibromohymenialdesine (dBHD) used to practice this invention is published by Prager and Tsopelas (R. H. Prager, C. Tsopelas; Aust. J. Chem.; Vol. 45, (1992), pp. 1771-1777), describing preparation of DBH through the use of aldisine 2. Condensation of 2 with 2-aminoimidazolinone under different conditions was unsuccessful, but esters 6 and 7 were prepared by reacting aldisine with diethyl malonate (DEM) in the presence of $TiCl_4$ (Scheme 3).

Scheme 3.

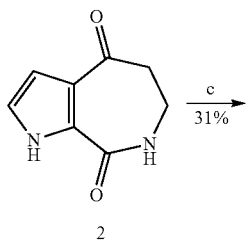

Another known synthesis that can be used to make dibromohymenialdesine (dBHD) used to practice this invention is published by Portevin, B., et al., *Tetrahedron Letters* (2003) 44 TETRAL 52 9263-9265. The Portevin scheme starts from pyrrole, and prepares aldisine 2 using the procedure described by (H. Cho, S. Matsuki, A. Mizuno, H. Annoura, T. Tatsuoka; *J. Heterocycl. Chem.*; Vol. 34, (1997), pp. 87-91) (Scheme 4).

Scheme 4.

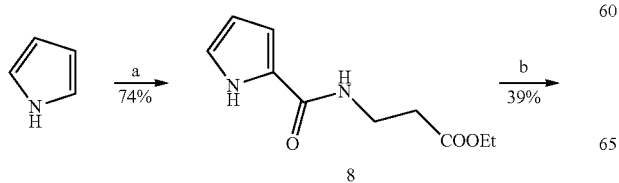

28

-continued

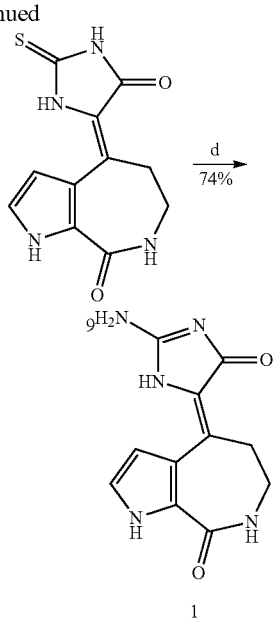

The Portevin scheme: Reagents and conditions: (a) (i). $Cl_3COCOCl$, dimethylaniline, toluene; (ii). $H_2NCH_2CH_2COOEt$, $CH_2Cl_2$; (b) (i). NaOH, EtOH; (ii). PPA, $P_2O_5$; (c) thiohydantoin, $BF_3.Et_2O$, $Et_3N$, THF; (d) $NH_4OH$, t-BuOOH, EtOH.

Pyrrole is reacted with diphosgene in the presence of dimethylaniline to give the acid chloride. Then a solution of ethyl 3-aminopropionate (or [beta]-alanine ethyl ester) is added in one-pot to give ester 8 in 74% yield for the two steps. Saponification (70%) is followed by cyclization in polyphosphoric acid (PPA) in the presence of a small amount of $P_2O_5$ to produce aldisine 2 in 56% yield on a 30 g scale. Aldisine is reacted with thiohydantoin in the presence of $TiCl_4$ and pyridine, but the intermediate 9 is only detected in trace amounts. Replacement of $TiCl_4$ with $BF_3.Et_2O$ in the presence of triethylamine gives 9 after chromatography in an unoptimized 31% yield. DBH can be obtained after chromatography in 74% yield by reacting 9 with aqueous ammonia in the presence of tert-butylhydroperoxide. In summary, the Portevin scheme starts is a very simple synthesis that allows the preparation of multigram quantities of DBH. Although several steps may need further optimization, this scheme also can be used to prepare DBH analogs of this invention, and DBH analogs used to practice the invention.

Example 4

The invention provides pharmaceutical compositions comprising dibromohymenialdesine (dBHD),

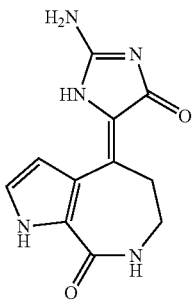

Figure 9:
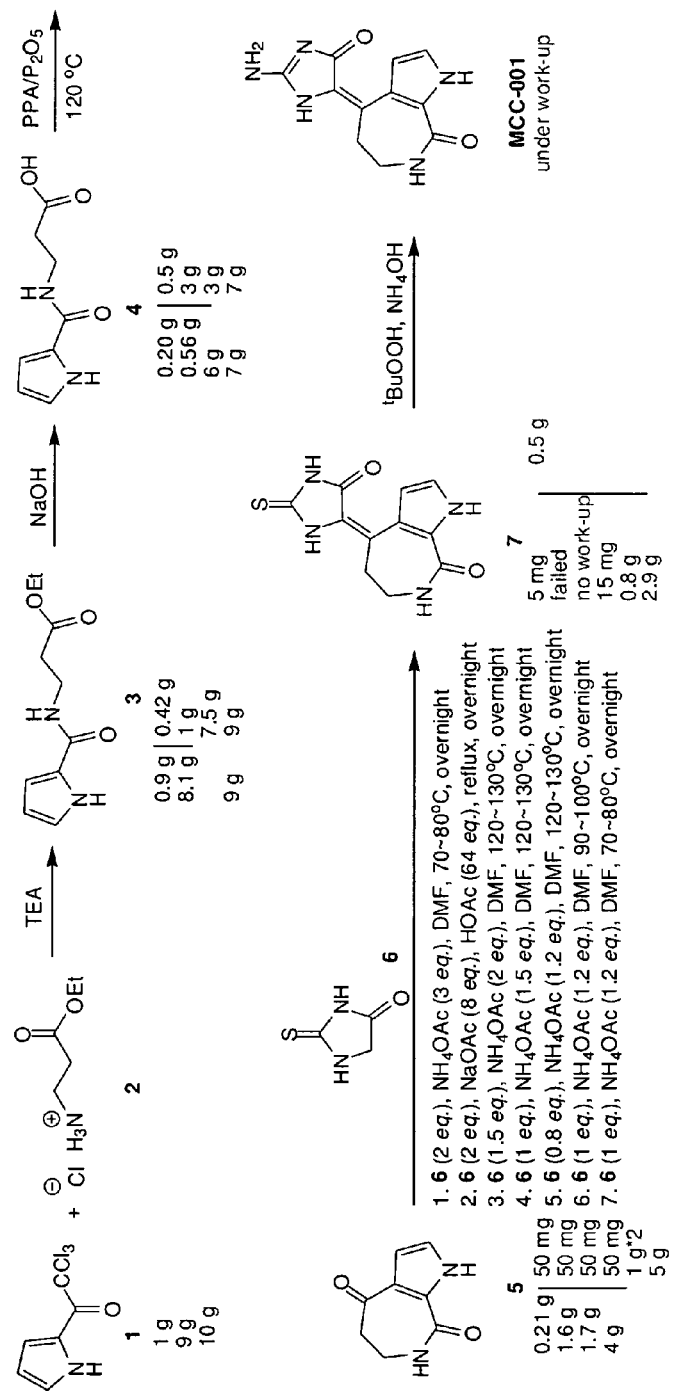
FIG. 9 describes exemplary methods for making compositions of the invention, as described in Example 4, below.

I and dBHD analogs, e.g., as described herein, and methods for making and using them. The invention also provides methods for making the compositions and pharmaceutical compositions of this invention, e.g., comprising protocols as illustrated in FIG. 9, also illustrated as this scheme:

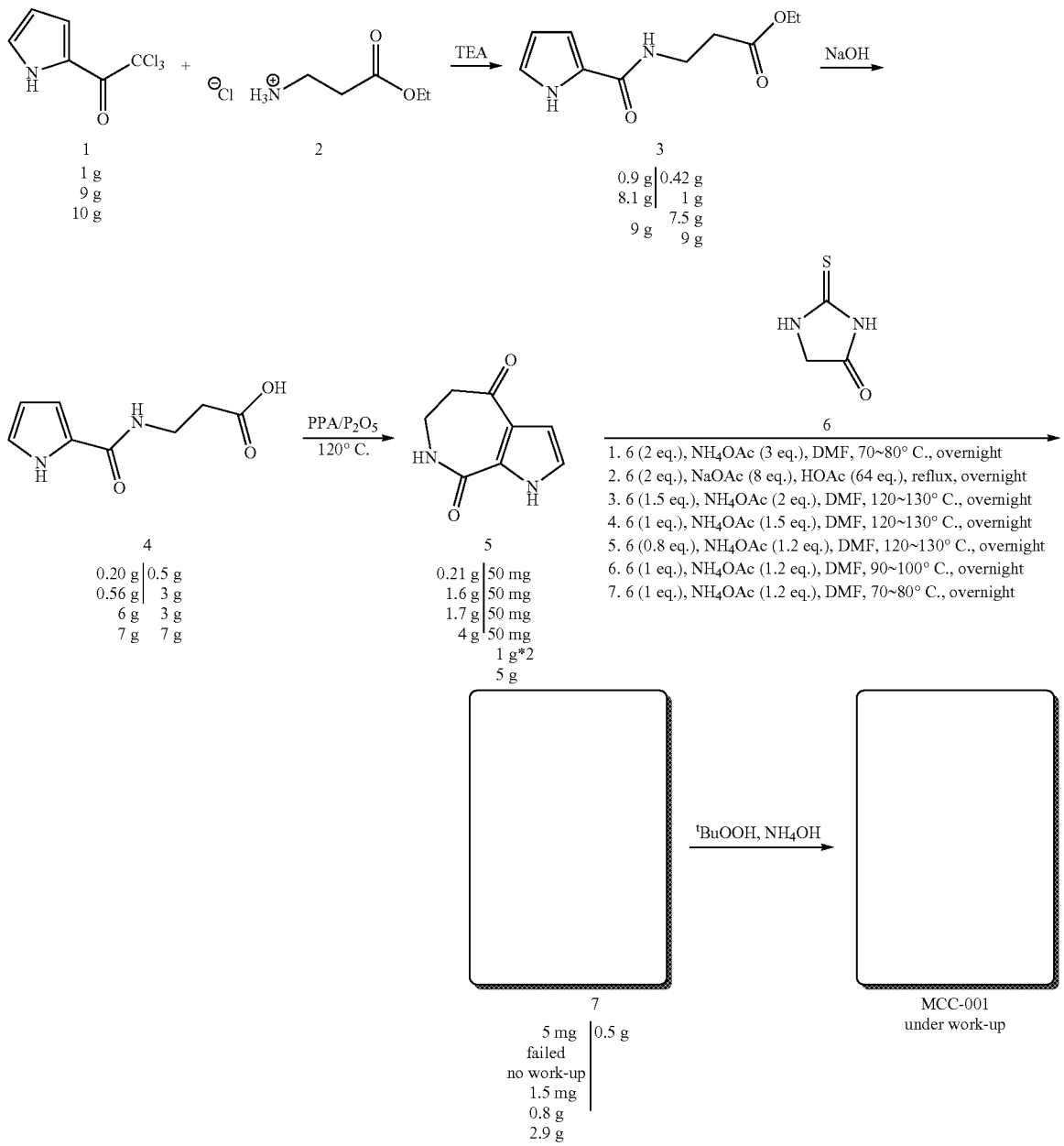

As shown in this scheme (above), after prep. HPLC purification, approximately 5 mg of 7 was obtained, Comparing condition 4 and condition 5, we found condition 4 was better, i.e., gave a higher yield: 15 mg of compound 7 was the yield in total from the two reactions.

The preparation following condition 6 and 7 was scaled up in parallel, and it was found that condition 6 was better; i.e., gave a higher yield: 0.8 g of 7 was obtained from the two batches. A second scaled up preparation of 7 gave a yield of 2.9 g, which was obtained from 5 g of 5.

A number of embodiments of the invention have been described. Nevertheless, it will be understood that various modifications may be made without departing from the spirit and scope of the invention. Accordingly, other embodiments are within the scope of the following claims.

What is claimed is:
1. A method for abrogating self-renewal of a leukemia cancer stem cell comprising:
  (a) providing:
    a pharmaceutical composition comprising a compound having a formula:

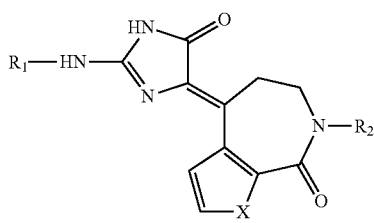

and wherein X is selected from the group consisting of NH, O, S and CH$_2$, and R$_1$ and/or the R$_2$ group are independently selected from the group consisting of a hydrogen, a halo, a hydroxy, a mercapto, a cyano, a formyl, an alkyl, heteroalkyl, heteroalkenyl, heteroalkynyl, a haloalkyl, an alkenyl, an alkynyl, an aryl, a substituted alkyl, alkenyl or alkynyl, an amino, a nitro, an alkoxy, a haloalkoxy, a thioalkoxy, an alkanoyl, a haloalkanoyl and a carboxy, wherein the "hetero" term refers to groups that contain one or more heteroatoms selected from the group consisting of O, S, N and combinations thereof, and, a pharmaceutically acceptable carrier; and (b) administering the pharmaceutical composition to a subject in need thereof.

2. The method of claim 1, wherein the pharmaceutical composition is formulated as a nanoparticle or a liposome or the pharmaceutical composition is delivered in vivo by a nanoparticle or a liposome.

3. The method of claim 1, wherein the compound is a debromohymenialdesine (dBHD).

4. The method of claim 1, further comprising co-administration of the pharmaceutical composition with a second drug or a pharmaceutical used for treating cancer or a related condition, or the composition is co-formulated with and/or co-administered with an analgesics, an antibiotics, a fluid, a cytokine, an immunoregulatory agent, an anti-inflammatory agent, a complement activating agent, a ficolin or a peptide or a protein comprising a collagen-like domain or a fibrinogen-like domain or a carbohydrate-binding domain.

5. The method of claim 1, wherein the pharmaceutical composition is formulated for parenteral administration or for intravenous (IV) administration or for administration into a body cavity or lumen of an organ.

6. A kit comprising a pharmaceutical composition and instructions for practicing a method for abrogating self-renewal of a leukemia stem cell, wherein the method comprises:

(a) providing:
a pharmaceutical composition comprising a compound having a formula:

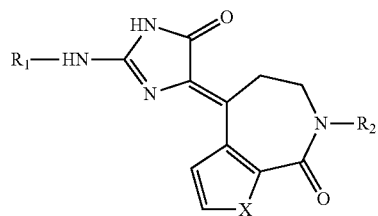

and wherein X is selected from the group consisting of NH, O, S and CH$_2$, and R$_1$ and/or the R$_2$, group are independently selected from the group consisting of a hydrogen, a halo, a hydroxy, a mercapto, a cyano, formyl, an alkyl, heteroalkyl, heteroalkenyl, heteroalkynyl, a haloalkyl, an alkenyl, an alkynyl, an aryl, a substituted alkyl, alkenyl or alkynyl, an amino, a nitro, an alkoxy, a haloalkoxy, a thioalkoxy, an alkanoyl, a haloalkanoyl and a carboxy, wherein the "hetero" term refers to groups that contain one or more heteroatoms selected from the group consisting of O, S, N and combinations thereof, and, a pharmaceutically acceptable carrier.

7. The method of claim 1, wherein the alkyl, haloalkyl, alkene, alkenyl in both or either of the R$_1$ and/or the R$_2$ groups is independently at least 1, 2, 3, 4, 5, 6, 7, 8, 9, 10, 11, 12, 13, 14, 15 or 16 carbons in length.

8. The method of claim 1, wherein the R$_1$ and/or the R$_2$ groups independently is a 5 membered ring or a 6 membered ring system.

9. The method of claim 8; wherein the 5 membered ring system is an imidazole, thiazole, triazole or oxadiazole, or the 6 membered ring system is a pyridine, a pyrimidine or a pyrazine.

* * * * *